United States Patent [19]

Caulk et al.

[11] 4,075,258

[45] Feb. 21, 1978

[54] ISOPARAFFIN OLEFIN ALKYLATION UTILIZING HIGH INTENSITY MIXING

[75] Inventors: Robert H. Caulk; David E. Allan, both of Baton Rouge, La.

[73] Assignee: Exxon Research & Engineering Co., Linden, N.J.

[21] Appl. No.: 708,058

[22] Filed: July 23, 1976

Related U.S. Application Data

[63] Continuation-in-part of Ser. No. 625,072, Oct. 23, 1975, Pat. No. 3,999,889.

[51] Int. Cl.² .............................................. C07C 3/54
[52] U.S. Cl. .......................... 260/683.44; 260/683.48; 260/683.53; 260/683.58; 260/683.59
[58] Field of Search ...................... 260/683.58, 683.59, 260/683.61, 683.53, 683.44

[56] References Cited

U.S. PATENT DOCUMENTS

| | | | |
|---|---|---|---|
| 2,459,636 | 1/1949 | Fenney | 260/683.59 |
| 2,463,262 | 3/1949 | Goldsby | 260/683.59 |
| 2,986,590 | 5/1961 | Knoble et al. | 260/683.59 |
| 3,133,975 | 5/1964 | Brewer et al. | 260/683.59 |
| 3,470,265 | 9/1969 | Sprow | 260/683.59 |

Primary Examiner—George Crasanakis
Attorney, Agent, or Firm—Llewellyn A. Proctor

[57] ABSTRACT

An improved process for the production of higher octane number products by the high intensity mixing of alkylation media, or media wherein olefins are alkylated by the addition thereto of isobutane. The alkylation reaction is conducted by contact between the reactants, which constitute a hydrocarbon phase, and an acid catalyst which constitutes an aqueous phase, the reactants being dispersed as an emulsion. It is found that when stirring an alkylation medium at above a certain threshold fluid mixing intensity, a $C_6+$ Motor Octane Number (MON) improvement ranging from about 0.5, and generally from about 0.5 to about 3.3, can be obtained by alkylating olefins with isobutane at high acid concentration while maintaining an acid soluble oil content ranging to about 3 percent, preferably from about 0.1 to about 3 percent, and more preferably from about 0.5 to about 2.5 percent, based on the weight of the reaction mixture, exclusive of the hydrocarbon phase. The alkylation is suitably conducted at acid strengths ranging from about 98 to about 88 percent, preferably from about 98 to about 94, based on the weight of the aqueous phase.

11 Claims, 5 Drawing Figures

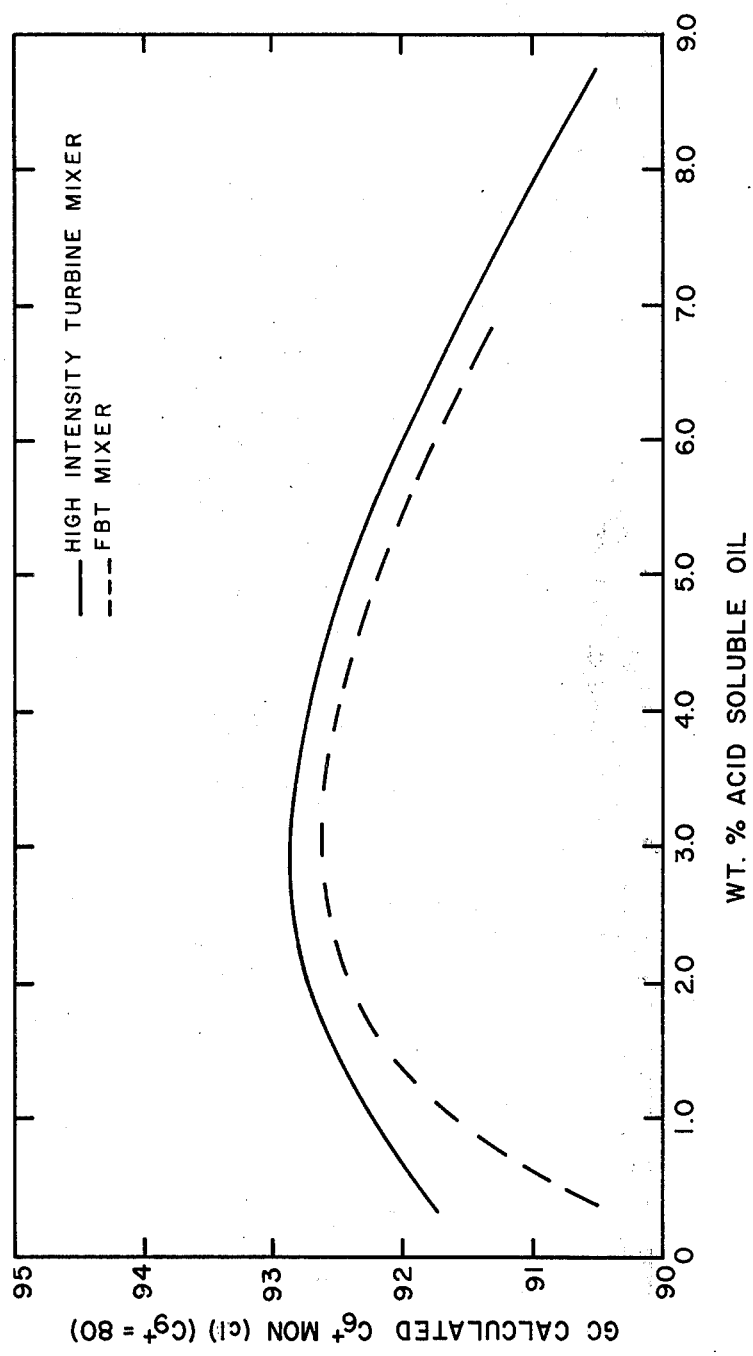

ISOPARAFFIN OLEFIN ALKYLATION UTILIZING HIGH INTENSITY MIXING

REFERENCE TO RELATED APPLICATIONS

This is a continuation-in-part of application Ser. No. 625,072, entitled "Mixing Head," filed Oct. 23, 1975 by Robert H. Caulk and Jerry E. Hankins, now U.S. Pat. 3,999,889. This application is herewith incorporated by reference.

Alkylation is a catalytic reaction involving the addition of a molecule of an isoparaffin to an olefin molecule. In the conventional alkylation process, isobutane is added to propene, butenes, pentenes or the like to produce high octane gasoline components. For example, a typical alkylation reaction involves the addition of butene-1 to isobutane to produce 2,2,4 trimethylpentane.

The alkylation reaction is conducted by contact between the reactants (hydrocarbon phase) and an acid catalyst (aqueous phase) wherein the two liquids are emulsified. Typically the alkylation catalyst comprises concentrated sulfuric acid, fluorosulfuric acid, hydrofluoric acid, aluminum chloride, boron fluoride, or the like, The reaction is typically conducted at temperatures ranging from about 30° F. to about 60° F. in a reactor comprising a series of vigorously stirred mixing compartments through which the isobutane-rich acid emulsion moves in series flow. Typically concentrated sulfuric acid, e.g., 98 wt. % sulfuric acid, is introduced into the first of the series of mixing compartments and spent alkylation acid, e.g., 88-92 wt. % acid, is withdrawn from the last mixing compartment of the series. The acid is not consumed in the chemical sense but is diluted by carbonaceous material and small amounts of water.

The reaction is exothermic, and the heat of reaction can be removed by auto-refrigeration resulting from vaporization of a portion of the reaction mixture. The reactor effluent emulsion is broken in a settler, providing a product hydrocarbon stream for fractionation and an acid stream which, after regeneration, is recycled to the reactor. Of several possible diluents that can affect acid strength, hence product quality, one of the most important is red oil or sludge, an acid soluble oil composed primarily of conjunct polymers which are highly unsaturated, ionized and contain numerous $C_5$ and $C_6$ rings. The red oil content of the acid, which increases as a function of processing time, is the primary cause of catalyst aging.

The alkylation reaction proceeds at practical rates only in an emulsion phase, or phase wherein fine droplets of the hydrocarbon phase are suspended in the aqueous phase. The mixing energy for providing and maintaining the emulsion phase is typically supplied by an impeller, of which there are various types and designs known in the chemical industries. Optimum mixing conditions require the formation of emulsions which have high interfacial area between the hydrocarbon and aqueous phases. High power input level supplied to an impeller of given geometry and style results in high flow rates and greater turbulence which enhances the rate of reaction and improves product quality by increasing motor octane numbers. However, better mixing, obtained by increased power consumption obviously has its limitations, particularly in that the amount of mixing achieved is not proportionate to the increased power input.

Of the various types of mixing devices known in the art, certain are superior to others in providing effective emulsification and good contact between immiscible liquids. A high shear turbine impeller, or mixing device, effective in alkylation processes is described by reference to application Ser. No. 625,072, supra, of which the instant application is a continuation-in-part. This mixer has proven particularly outstanding as contrasted with, e.g., the flat blade turbine, which has become the commercial standard bearer for the chemical and petroleum industry. Tests have shown that when these high intensity mixers are employed in an alkylation process, better mixing of the alkylation medium is achieved and, at constant acid soluble oil level, as much as about 0.5 $C_6+$ Motor Octane Number (MON) advantage is obtained at identical power input level, as contrasted with the use of a flat bladed turbine mixer. Whereas such improvements were not expected as a result of employing the high intensity impeller in an alkylation medium, Applicants were particularly surprised to learn that even greater octane improvement could be provided by various other changes in process conditions, taken in conjunction with high intensity stirring.

It is, accordingly, the primary objective of the present invention to provide an improved alkylation process, particularly an alkylation process operated at conditions, inclusive of high fluid intensity mixing, which produces products of improved quality.

A specific object is to produce an alkylation process of such character wherein an alkylate of improved octane is obtained.

These objects and others are achieved in accordance with the present invention which is based on the discovery that, in the alkylation of olefins by the addition thereto of isobutane, a correlation exists between the acid strength, product quality and the intensity of mixing the hydrocarbon and aqueous acid phases. In accordance therewith, it is found that when stirring an alkylation medium at above a certain threshold fluid mixing intensity, a $C_6+$ Motor Octane Number (MON) improvement ranging from about 0.5 and generally from about 0.5 to about 3.3, can be obtained by alkylating olefins with isobutane at high acid concentration while maintaining an acid soluble oil content ranging to about 3 percent, preferably from about 0.1 to about 3 percent, and more preferably from about 0.5 to about 2.5 percent, based on the weight of the reaction mixture, exclusive of the hydrocarbon phase. The alkylation is suitably conducted at acid strengths ranging from about 98 to about 88 percent, preferably from about 98 to about 94, based on the weight of the aqueous phase.

The level of mixing achieved with any stirrer can be quantified in several ways, but quantification in terms of power consumption provides a very practical measurement. It is thus known that the mixing energy supplied to an alkylation medium, given a specific type and stirrer design, is directly affected by the level of power input, P, and by stirrer speed, N. The level of power input, P, is directly proportional to the cube of the stirrer speed, i.e., $P \alpha N^3$. The quantity of flow, Q, and the level of turbulence, H, are also directly related to stirrer speed, i.e., $Q \alpha N$ and $H \alpha N^2$. From these values it can be determined that $P = \pi QH$ where $\pi$ represents the density of the medium. The density of the medium is substantially unity. Applicants have perceived an important relationship between Q and H, at any given power input level P, and have established that important process advantages can be obtained by design of a stirrer to provide, at constant power input, a high turbulence head, H, relative to the flow, Q, particularly when the alkylation media is maintained at high acid level concentration during the stirring. In practical terms, the mixing level achieved by the prior art flat bladed turbine is taken as a suitable standard, and equated with unity, at constant power input level. Applicants have learned that better mixing, or values of H greater than unity, provide higher octane, at constant power input, particularly in high strength acid alkylation media which contains low acid soluble oil contents, and that as the turbulence head, or value of H, is increased from greater than 1.0, suitably greater than 1.0 to about 3, and preferably greater than 1 to about 2, even greater improvements are obtained.

The process of this invention requires the use of a high intensity impeller and can be best illustrated by that disclosed and claimed in application Ser. No. 625,072, supra, a highly preferred mixing device for the practice of this invention which is contrasted with the commercial flat bladed turbine mixer taken as the prior art standard. In view of the importance of these devices, each will be described in detail prior to further description of the process.

Referring to the drawings:

FIG. 1 is an isometric view of the commercially known flat bladed turbine (FBT) mixer, various physical dimensions essential to the stirring quality of the mixer being designated alphabetically.

FIG. 2 schematically depicts the FBT mixer mounted within a mixing compartment (or zone) of a series contained within an alkylation reactor. The diameter of the compartment, an additional physical measurement from those characterized in FIG. 1, is designated alphabetically.

FIG. 5 is a schematic diagram showing the advantages obtained by use of the high intensity turbine mixer used for stirring alkylation media.

Figure 1:
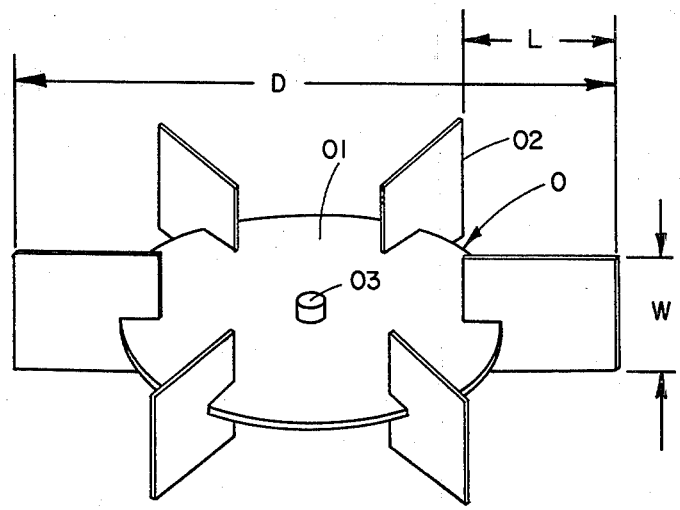

Referring to FIG. 1, the flat bladed turbine mixer 0 is characterized as comprised of a disc 01 at the peripheral edge of which is mounted, in a plane perpendicular to that of the disc, a plurality of evenly spaced, parallelly aligned, radially extended paddles or blades 02 ($02_1$. . . $02_6$), and at the center of which is located a hub 03 within which a shaft 04 can be affixed for transmission of power thereto from a prime mover 05 (FIG. 2), suitably an electric motor. Each of the blades of the FBT mixer is characterized as of width W, of length L, and the FBT mixer has a diameter of D.

Figure 2:
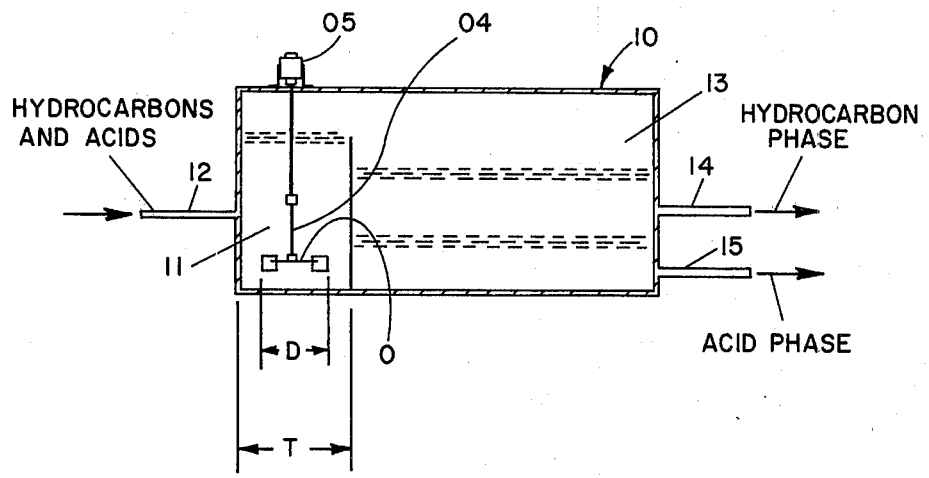

With reference to FIG. 2, this sketch schematically depicts an alkylation reactor 10, inclusive of a first compartment (or zone) 11, of diameter T, of a series (not shown) within which the FBT mixer is mounted, and within which hydrocarbon and acid streams are introduced. In accordance therewith, hydrocarbons and acid are introduced into compartment 11 via line 12, the emulsion phase overflowing into a quiescent zone 13 wherein the hydrocarbon and acid phases are stratified and from which the hydrocarbon phase is withdrawn via line 14, and the acid phase via line 15.

In conducting the alkylation reaction, generally from about 5 to about 11 compartments are provided in a single reactor. Reactors can be employed in series or in parallel, or both, and individual reactors can be staged or non-staged. In a given reactor, or reactor section, the alkylation reaction is conducted at temperatures ranging from about 20° F to about 80° F, preferably from about 40° F to about 50° F, and a residence time within each compartment ranging from about 1 to about 10 minutes, preferably from about 2 to 5 minutes, is provided. The acid strength within the several compartments of a given reactor, or several sections wherein several reaction vessels are employed in series, generally ranges from about 98 percent in the lead compartment (or lead reactor section) to about 88 percent in the last compartment in the series, based on the weight of the aqueous phase. Typical alkylation catalysts comprise concentrated sulfuric acid, hydrofluoric acid, aluminum chloride, boron fluoride, and the like. Suitably, the acid-to-hydrocarbon ratio in a given reaction medium ranges from about 1:1 to about 3:1, preferably from about 1.5:1 to about 2.3:1, based on volume.

Figure 3:
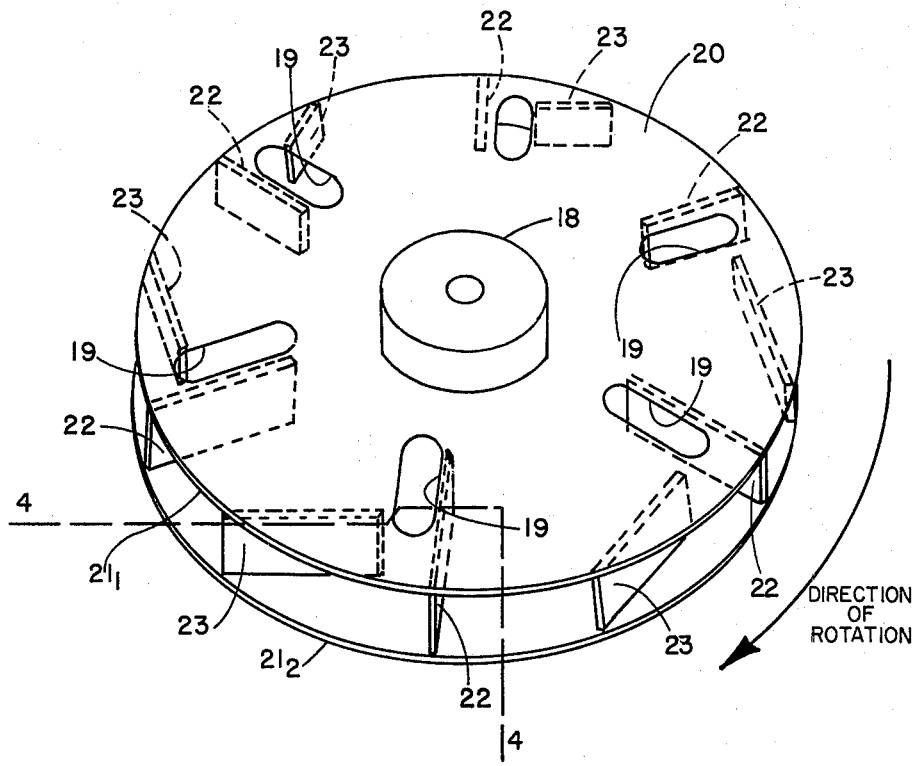
FIG. 3 is an isometric view of the high intensity turbine mixer disclosed and claimed in application Ser. No. 625,072.
Figure 4:
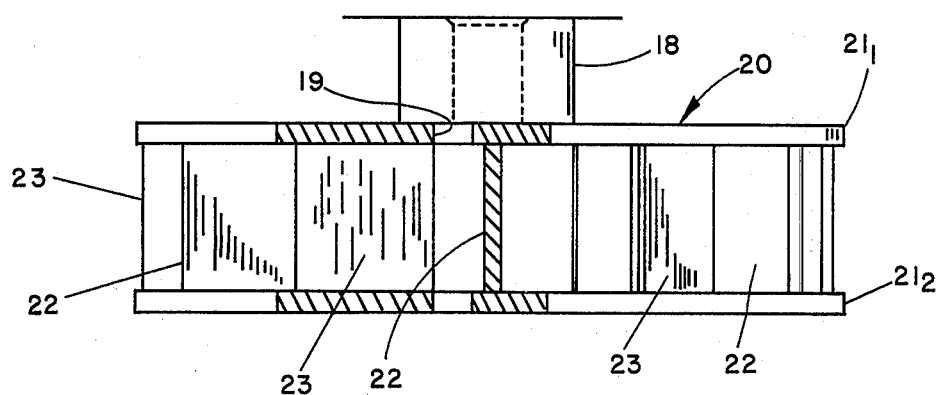
FIG. 4 is a section view taken along line 3—3 of FIG. 3.

Referring to FIGS. 3 and 4, there is described a preferred high intensity mixing head 20 having a hub 18 for operative connection to a rotatable shaft (not shown), such that the mixing head can be rotated at speed suitable for providing high local fluid agitation and high surface areas, at low power inputs. The mixing head 20, in brief, is characterized as comprised of an adjoined pair of coaxially aligned, spaced discs 21 ($21_1$,$21_2$) of similar size, geometric configuration and shape, a plurality of radially extended slots 19 ($19_1$. . . $19_6$) located upon the upwardly faced disc 21, the radial length of each of which is relatively long as contrasted with its width. For optimum balance of turbulence and flow the length:width of a slot 19 ranges to about 4, preferably from about 3 to 4; and the length of a slot ranges from about ⅛ to about 1/12 of the diameter of the mixing head. Compartments are formed between the spaced discs 21 via a plurality of blade pairs 22,23 associated with each of the radial slots 19, suitably at least four blade pairs, and preferably at least six blade pairs; one blade 22 of a pair of which extends substantially from the circumference or peripheral edge of the discs 21 along the radius, a distance of from about ½ to about 4/5 of the radius, while the other blade of the pair is mounted on the opposite side of a slot 19 in direction perpendicular thereto and extended from the circumference or peripheral edge of the discs 21 to an outer edge of a slot 19. Thus, compartments are formed by radially extending blades 22 located alongside the trailing edge of a slot 19, and it is extended from, and suitably adjoined to, the trailing edge (as determined by the direction of rotation) of a radial slot 19 of one disc $21_1$ across to the corresponding trailing edges of the aligned radial slots 19 of the other $21_2$, and by a plurality of blades 23 perpendicularly extended from the leading edges of said aligned paired slots 19 to peripheral edges of said discs 21. The presence of the blades 23, mounted in perpendicular orientation relative to the slots 19, with optimization of slot size, is required for high fluid intensities. In operation, rotation of the mixing head 20 forces fluids through the slots 19 from above and below the discs 21 to provide great turbulence and mixing of the liquids, per unit of power input. Turbulently, intensively mixed liquids are pumped out of the mixing head 20 at high velocities in a radial direction outwardly from said mixing head.

Applicants have found that, at any given power input level P, they can alter the geometrical shape and style of an impeller to change the level of mixing intensity achieved in any given compartment to increase the magnitude of the turbulent head, H, relative to flow, Q, with corresponding improvements in octane. They have also discovered that the octane improvement achieved is disproportionately higher when the value of H is increased relative to Q in compartments which contain high acid concentration vis-a-vis compartments which contain low acid concentration, particularly when the acid soluble oil content of the acid phase is relatively low. The relative values of Q and H at a constant power input level of one, or unity, for the two types of mixers, i.e., the FBT mixer described by reference to FIGS. 1-2 and the high intensity mixer described with reference to FIGS. 3-4, and modified versions thereof, are characterized in Table I wherein W = width and L = length of a blade, D = diameter of the mixing head, and T = diameter of the compartment.

With reference to Table I it will thus be observed that the value of H is unity for the FBT mixer (Mixer A), the commercial standard bearer, or specifically in the formula P = QH the value of P, Q and H are each of unit value. By modification of the physical Whereas Applicants have no desire to be bound by any specific theory of mechanism, it is believed that increased turbulence, H, relative to the flow, Q, provides improved octane due at least in part to the effect of increased turbulence on emulsion drop size. The presence of the acid-soluble oil at these conditions, increases the effectiveness of the acid catalyst. The acid soluble oil acts both as a hydride transfer agent and as a surfactant. It tends to enhance emulsification between the hydrocarbon and aqueous phases. As the concentration of the acid soluble oil increases beyond about 3 percent, based on the weight of the aqueous phase, however, dilution of the acid occurs and the octane improvement is decreased. Quite obviously, therefore, in view of experimental data, the advantages of the better mixing achieved by impeller modifications are most prevalent when such mixers are employed in that portion of the process wherein the acid catalyst concentration is high, and wherein the acid soluble oil content is low.

It is apparent that various modifications can be made to alter the dimensions, geometry and style of an impel-

TABLE I

| Impeller[1] | Designation | D | W | L | W/D | D/T | P | Q | H |
|---|---|---|---|---|---|---|---|---|---|
| FBT Mixer (Standard) | A | 0.178 | 0.0356 | 0.045 | 0.20 | 0.59 | 1 | 1 | 1 |
| FBT Mixer (Modified) | B | 0.15 | 0.050 | 0.0475 | 0.25 | 0.50 | 1 | .634 | 1.57 |
| FBT Mixer (Modified) | C | 0.10 | 0.050 | 0.0315 | 0.50 | 0.33 | 1 | .215 | 4.65 |
| FBT Mixer (Modified) | D | 0.10 | 0.025 | 0.0315 | 0.25 | 0.33 | 1 | .159 | 6.29 |
| High Intensity Turbine Mixier[2] | E | 0.178 | 0.0356 | — | 0.20 | 0.59 | 1 | 0.59 | 1.70 |
| High Intensity Turbine Mixer[3] | F | 0.10 | 0.025 | — | 0.25 | 0.33 | 1 | 0.094 | 10.66 |

[1] T = 0.30 meters. The power input is a measure of the energy, or horsepower, applied to an impeller. In a given service, the power input level is measured by the formula:

$$H.P. = \frac{N_p \times D^5 \times \rho N^3}{17,710}$$

wherein H.P. is horsepower, N is the impeller speed in revolutions per second, D is the impeller diameter in feet, and $\rho$ is the fluid density in pounds per cubic feet which is substantially equal to one. For any given power input, both sides of the equation P = QH are divided by the power input to provide a unit value for P. Q × H thus also becomes of unit value, though when H is increased, Q is decreased and vice versa.

[2] Distance, in meters, m, between two coaxial discs, the thickness of each of which was 0.00159 m. was 0.0324 m; the mixing head was comprised of 6 pairs of blades, 0.0445 m × 0.0324 m each. The slot size was 0.0254 m × 0.0074 m.
[3] Scaled according to specifications in Serial No. 625,072.

dimensions of either the standard FBT mixer (to provide Mixers B,C,D) or by use of a high intensity turbine mixer, as in a compartment of given diameter, however, the value of H can be increased relative to Q, which is proportionately decreased.

EXAMPLE

By way of example, referring to FIG. 5, first specifically to the curve shown by a dashed line, there is graphically illustrated the results obtained by use of Mixer A at sulfuric acid strengths ranging 98 percent to 88 percent (2-3 percent water) and given acid soluble oil levels (x-axis) as a function of $C_6+$ Motor Octane Number (MON) (y-axis). In conducting the tests, the acid-to-hydrocarbon ratio is maintained at 2.1:1 (volumetric), and temperature at 40° F, wherein mixed butenes are reacted with excess isobutane within the alkylation medium to produce primarily 2,2,4-trimethylpentane and other alkylation products. This curve, obtained by use of Mixer A, is sharply contrasted with that formed hy Mixer E (solid curved line) under identical conditions. It is apparent by reference to the curves that an octane improvement results over the whole length of acid level concentration by use of the high intensity turbine mixer, or Mixer E, but particularly between a sulfuric acid concentration ranging from about 98 to about 94 Wt.%, and at an acid soluble oil level ranging below 3.0. A similar curve was obtained under conditions otherwise identical except that fluorosulfuric acid was substituted as the catalyst.

ler, as well as that of the compartment within which the alkylation is conducted, to increase the levels of turbulence relative to flow, at constant power input, and to employ impellers having such characteristics within high acid, low acid soluble oil alkylation media to improve alkylation process characteristics. Accordingly, such modifications as would be apparent to those of skill in the art are encompassed and within the spirit and scope of the present invention.

Having described the invention, what is claimed is:

1. In an alkylation process wherein a hydrocarbon phase, inclusive of an isoparaffin and olefin, is contacted with an acid catalyst in aqueous phase to produce an acid soluble oil and alkylation products, and wherein said hydrocarbon and aqueous phases are agitated, mixed and dispersed as an emulsion of said phases by use of a mixing apparatus, the head of said apparatus being inserted within the hydrocarbon and aqueous phases and rotated, the improvement comprising agitating said phases with said mixing apparatus, said head comprising a pair of coaxially aligned upper and and lower discs of similar size, geometric configuration and shape, a plurality of radially extended slots through said upper disc, the length of each slot being relatively long as contrasted with its width, compartments being formed between the spaced discs by a plurality of blade pairs associated with each of said radial slots, one blade of a pair being extended substantially from the peripheral edge of said discs along the radius thereof for a distance of from 178 to about one-fourth of the radius, while the other blade of the pair being extended from the opposite side of a slot in a direction perpendicular to said radius and extended from the peripheral edge of the disc to the edge of said slot while maintaining the acid strength of the aqueous phase at concentration ranging from about 98 to 94 percent, and an acid soluble oil concentration ranging from about 0.5 to about 3 percent, based on the weight of the aqueous phase.

2. The process of claim 1 wherein the hydrocarbon phase is comprised of isobutane and a compound selected from propene, butenes, and pentenes.

3. The process of claim 1 wherein the aqueous phase is comprised of sulfuric acid, hydrofluoric acid, aluminum chloride, and boron fluoride.

4. The process of claim 1 wherein the aqueous and hydrocarbon phases are contacted in acid-to-hydrocarbon ratio ranging from about 1:1 to about 3:1, on a volume basis.

5. The process of claim 1 wherein the acid soluble oil content of the aqueous phase ranges from about 0.5 to about 2.5 percent, based on the weight of the aqueous phase.

6. The process of claim 1 wherein the temperature of the emulsion is maintained at from about 20° F to about 80° F.

7. The process of claim 5 wherein the temperature ranges from about 40° F to about 50° F, and the emulsion is constituted in part of an aqueous phase of sulfuric acid or fluorosulfuric acid.

8. The process of claim 1 wheren the length:width of each slot ranges to about 4.

9. The process of claim 1 wherein the length:width of each slot ranges from about 3 to 4.

10. The process of claim 1 wherein the length of each slot ranges from about ⅛ to about 1/12 of the diameter of the mixing head.

11. The process of claim 1 wherein the plurality of blade pairs is at least 4.

* * * * *